(12) United States Patent
Huang et al.

(10) Patent No.: US 7,886,419 B2
(45) Date of Patent: Feb. 15, 2011

(54) STENT CRIMPING APPARATUS AND METHOD

(75) Inventors: Bin Huang, Pleasanton, CA (US); David C. Gale, San Jose, CA (US); Daniel Castro, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1113 days.

(21) Appl. No.: 11/489,309

(22) Filed: Jul. 18, 2006

(65) Prior Publication Data

US 2008/0016668 A1   Jan. 24, 2008

(51) Int. Cl.
*G01M 19/00* (2006.01)
*B23Q 3/00* (2006.01)

(52) U.S. Cl. .......... 29/407.08; 29/515; 29/516; 29/283

(58) Field of Classification Search .......... 29/407.08, 29/407.09, 407.1, 505, 515, 516, 282, 283, 29/283.5
See application file for complete search history.

(56) References Cited

U.S. PATENT DOCUMENTS

| | | | |
|---|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |

(Continued)

FOREIGN PATENT DOCUMENTS

DE   44 07 079   9/1994

(Continued)

OTHER PUBLICATIONS

International Search Report for PCT/US2007/016200, filed Jul. 17, 2007, mailed Nov. 21, 2007, 5 pgs.

(Continued)

*Primary Examiner*—Essama Omgba
(74) *Attorney, Agent, or Firm*—Suire, Sanders & Dempsey LLP.

(57) ABSTRACT

A method for crimping a stent onto a balloon includes inflating a balloon with a fluid, sliding a stent over the inflated balloon, crimping the stent onto the balloon, and controlling the pressure inside the balloon below a given value when the stent is being crimped onto the balloon.

21 Claims, 3 Drawing Sheets

U.S. PATENT DOCUMENTS

| | | |
|---|---|---|
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,147,385 A | 9/1992 | Beck et al. |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,292,321 A | 3/1994 | Lee |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,546,646 A * | 8/1996 | Williams et al. ......... 29/407.08 |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,836,965 A | 11/1998 | Jendersee et al. |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,913,871 A | 6/1999 | Werneth et al. |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |

| | | | | | | |
|---|---|---|---|---|---|---|
| 5,954,744 | A | 9/1999 | Phan et al. | 6,312,459 | B1 | 11/2001 | Huang et al. |
| 5,957,975 | A | 9/1999 | Lafont et al. | 6,327,772 | B1 | 12/2001 | Zadno-Azizi et al. |
| 5,965,720 | A | 10/1999 | Gryaznov et al. | 4,733,665 | C2 | 1/2002 | Palmaz |
| 5,971,954 | A | 10/1999 | Conway et al. | 6,375,826 | B1 | 4/2002 | Wang et al. |
| 5,971,992 | A * | 10/1999 | Solar .......................... 606/108 | 6,379,381 | B1 | 4/2002 | Hossainy et al. |
| 5,976,181 | A * | 11/1999 | Whelan et al. ............. 623/1.12 | 6,387,121 | B1 | 5/2002 | Alt |
| 5,976,182 | A | 11/1999 | Cox | 6,388,043 | B1 | 5/2002 | Langer et al. |
| 5,980,564 | A | 11/1999 | Stinson | 6,395,326 | B1 | 5/2002 | Castro et al. |
| 5,980,928 | A | 11/1999 | Terry | 6,409,761 | B1 | 6/2002 | Jang |
| 5,980,972 | A | 11/1999 | Ding | 6,423,092 | B2 | 7/2002 | Datta et al. |
| 5,981,568 | A | 11/1999 | Kunz et al. | 6,461,632 | B1 | 10/2002 | Gogolewski |
| 5,986,169 | A | 11/1999 | Gjunter | 6,464,720 | B2 | 10/2002 | Boatman et al. |
| 5,997,468 | A | 12/1999 | Wolff et al. | 6,479,565 | B1 | 11/2002 | Stanley |
| 6,009,614 | A * | 1/2000 | Morales ....................... 29/516 | 6,485,512 | B1 | 11/2002 | Cheng |
| 6,010,445 | A | 1/2000 | Armini et al. | 6,492,615 | B1 | 12/2002 | Flanagan |
| 6,015,541 | A | 1/2000 | Greff et al. | 6,494,908 | B1 | 12/2002 | Huxel et al. |
| 6,042,875 | A | 3/2000 | Ding et al. | 6,495,156 | B2 | 12/2002 | Wenz et al. |
| 6,048,964 | A | 4/2000 | Lee et al. | 6,511,748 | B1 | 1/2003 | Barrows |
| 6,051,648 | A | 4/2000 | Rhee et al. | 6,517,888 | B1 | 2/2003 | Weber |
| 6,056,993 | A | 5/2000 | Leidner et al. | 6,527,801 | B1 | 3/2003 | Dutta |
| 6,060,451 | A | 5/2000 | DiMaio et al. | 6,537,589 | B1 | 3/2003 | Chae et al. |
| 6,063,092 | A * | 5/2000 | Shin ........................... 606/108 | 6,539,607 | B1 | 4/2003 | Fehring et al. |
| 6,066,156 | A | 5/2000 | Yan | 6,540,777 | B2 | 4/2003 | Stenzel |
| 6,071,266 | A | 6/2000 | Kelley | 6,554,854 | B1 | 4/2003 | Flanagan |
| 6,074,659 | A | 6/2000 | Kunz et al. | 6,565,599 | B1 | 5/2003 | Hong |
| 6,080,177 | A | 6/2000 | Igaki et al. | 6,569,191 | B1 | 5/2003 | Hogan |
| 6,080,488 | A | 6/2000 | Hostettler et al. | 6,569,193 | B1 | 5/2003 | Cox et al. |
| 6,083,258 | A | 7/2000 | Yadav | 6,572,672 | B2 | 6/2003 | Yadav et al. |
| 6,093,463 | A | 7/2000 | Thakrar | 6,574,851 | B1 | 6/2003 | Mirizzi |
| 6,096,070 | A | 8/2000 | Ragheb et al. | 6,579,305 | B1 | 6/2003 | Lashinski |
| 6,096,525 | A | 8/2000 | Patnaik | 6,585,755 | B2 | 7/2003 | Jackson et al. |
| 6,099,562 | A | 8/2000 | Ding et al. | 6,592,614 | B2 | 7/2003 | Lenker et al. |
| 6,103,230 | A | 8/2000 | Billiar et al. | 6,592,617 | B2 | 7/2003 | Thompson |
| 6,107,416 | A | 8/2000 | Patnaik et al. | 6,613,072 | B2 | 9/2003 | Lau et al. |
| 6,110,188 | A | 8/2000 | Narciso, Jr. | 6,626,939 | B1 | 9/2003 | Burnside et al. |
| 6,113,629 | A | 9/2000 | Ken | 6,635,269 | B1 | 10/2003 | Jennissen |
| 6,117,979 | A | 9/2000 | Hendriks et al. | 6,645,243 | B2 | 11/2003 | Vallana et al. |
| 6,120,536 | A | 9/2000 | Ding et al. | 6,656,162 | B2 | 12/2003 | Santini, Jr. et al. |
| 6,120,904 | A | 9/2000 | Hostettler et al. | 6,664,335 | B2 | 12/2003 | Krishnan |
| 6,121,027 | A | 9/2000 | Clapper et al. | 6,666,214 | B2 | 12/2003 | Canham |
| 6,125,523 | A | 10/2000 | Brown et al. | 6,666,880 | B1 * | 12/2003 | Chiu et al. .................. 623/1.11 |
| 6,127,173 | A | 10/2000 | Eckstein et al. | 6,667,049 | B2 | 12/2003 | Janas et al. |
| 6,129,761 | A | 10/2000 | Hubbell | 6,669,723 | B2 | 12/2003 | Killion et al. |
| 6,129,928 | A | 10/2000 | Sarangapani et al. | 6,676,697 | B1 | 1/2004 | Richter |
| 6,150,630 | A | 11/2000 | Perry et al. | 6,679,980 | B1 | 1/2004 | Andreacchi |
| 6,153,252 | A | 11/2000 | Hossainy et al. | 6,689,375 | B1 | 2/2004 | Wahlig et al. |
| 4,776,337 | A | 12/2000 | Palmaz | 6,695,920 | B1 | 2/2004 | Pacetti et al. |
| 6,159,951 | A | 12/2000 | Karpeisky et al. | 6,706,273 | B1 | 3/2004 | Roessler |
| 6,160,084 | A | 12/2000 | Langer et al. | 6,709,379 | B1 | 3/2004 | Brandau et al. |
| 6,165,212 | A | 12/2000 | Dereume et al. | 6,719,934 | B2 | 4/2004 | Stinson |
| 6,166,130 | A | 12/2000 | Rhee et al. | 6,719,989 | B1 | 4/2004 | Matsushima et al. |
| 6,169,170 | B1 | 1/2001 | Gryaznov et al. | 6,720,402 | B2 | 4/2004 | Langer et al. |
| 6,171,609 | B1 | 1/2001 | Kunz | 6,745,445 | B2 * | 6/2004 | Spilka ...................... 29/407.08 |
| 6,174,330 | B1 | 1/2001 | Stinson | 6,746,773 | B2 | 6/2004 | Llanos et al. |
| 6,177,523 | B1 | 1/2001 | Reich et al. | 6,752,826 | B2 | 6/2004 | Holloway et al. |
| 6,183,505 | B1 | 2/2001 | Mohn, Jr. et al. | 6,753,007 | B2 | 6/2004 | Haggard et al. |
| 6,187,045 | B1 | 2/2001 | Fehring et al. | 6,764,505 | B1 | 7/2004 | Hossainy et al. |
| 6,210,715 | B1 | 4/2001 | Starling et al. | 6,769,161 | B2 * | 8/2004 | Brown et al. .................. 29/234 |
| 6,224,626 | B1 | 5/2001 | Steinke | 6,818,063 | B1 | 11/2004 | Kerrigan |
| 6,228,845 | B1 | 5/2001 | Donovan et al. | 6,846,323 | B2 | 1/2005 | Yip et al. |
| 6,240,616 | B1 | 6/2001 | Yan | 6,863,683 | B2 * | 3/2005 | Schwager et al. .......... 623/1.11 |
| 6,245,076 | B1 | 6/2001 | Yan | 6,958,073 | B2 * | 10/2005 | Rogers et al. ............... 606/194 |
| 6,245,103 | B1 | 6/2001 | Stinson | 7,008,446 | B1 | 3/2006 | Amis et al. |
| 6,248,344 | B1 | 6/2001 | Ylanen et al. | 7,563,400 | B2 * | 7/2009 | Wilson et al. ............... 264/249 |
| 6,251,135 | B1 | 6/2001 | Stinson et al. | 2001/0044652 | A1 | 11/2001 | Moore |
| 6,251,142 | B1 | 6/2001 | Bernacca et al. | 2002/0002399 | A1 | 1/2002 | Huxel et al. |
| 6,273,913 | B1 | 8/2001 | Wright et al. | 2002/0004060 | A1 | 1/2002 | Heublein et al. |
| 6,281,262 | B1 | 8/2001 | Shikinami | 2002/0004101 | A1 | 1/2002 | Ding et al. |
| 6,284,333 | B1 | 9/2001 | Wang et al. | 2002/0062148 | A1 | 5/2002 | Hart |
| 6,287,332 | B1 | 9/2001 | Bolz et al. | 2002/0065553 | A1 | 5/2002 | Weber |
| 6,290,721 | B1 | 9/2001 | Heath | 2002/0111590 | A1 | 8/2002 | Davila et al. |
| 6,293,966 | B1 | 9/2001 | Frantzen | 2002/0116050 | A1 | 8/2002 | Kocur |
| 6,303,901 | B1 | 10/2001 | Perry et al. | 2002/0138133 | A1 | 9/2002 | Lenz et al. |

| | | | |
|---|---|---|---|
| 2002/0161114 A1 | 10/2002 | Gunatillake et al. | |
| 2003/0033001 A1 | 2/2003 | Igaki | |
| 2003/0055482 A1 | 3/2003 | Schwager et al. | |
| 2003/0056360 A1 | 3/2003 | Brown et al. | |
| 2003/0093107 A1 | 5/2003 | Parsonage et al. | |
| 2003/0100865 A1 | 5/2003 | Santini, Jr. et al. | |
| 2003/0105518 A1 | 6/2003 | Dutta | |
| 2003/0105530 A1 | 6/2003 | Pirhonen | |
| 2003/0171053 A1 | 9/2003 | Sanders | |
| 2003/0187495 A1 | 10/2003 | Cully et al. | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236563 A1 | 12/2003 | Fifer | |
| 2004/0078953 A1 | 4/2004 | Spilka | |
| 2004/0093077 A1 | 5/2004 | White et al. | |
| 2004/0098095 A1 | 5/2004 | Burnside et al. | |
| 2004/0111149 A1 | 6/2004 | Stinson | |
| 2004/0127970 A1 | 7/2004 | Weber | |
| 2004/0143317 A1 | 7/2004 | Stinson et al. | |
| 2004/0167610 A1 | 8/2004 | Fleming, III | |
| 2005/0143752 A1* | 6/2005 | Schwager et al. | 606/108 |
| 2006/0009832 A1* | 1/2006 | Fisher | 623/1.11 |
| 2006/0047336 A1 | 3/2006 | Gale et al. | |
| 2006/0142834 A1* | 6/2006 | Rizq et al. | 623/1.11 |
| 2006/0288561 A1* | 12/2006 | Roach et al. | 29/508 |
| 2007/0006441 A1* | 1/2007 | McNiven et al. | 29/508 |
| 2007/0129786 A1* | 6/2007 | Beach et al. | 623/1.15 |
| 2007/0204455 A1* | 9/2007 | Knott et al. | 29/508 |
| 2007/0289117 A1* | 12/2007 | Huang et al. | 29/508 |
| 2008/0001328 A1* | 1/2008 | Kent et al. | 264/268 |
| 2008/0028594 A1* | 2/2008 | Lafont et al. | 29/516 |
| 2009/0088829 A1* | 4/2009 | Wang et al. | 623/1.11 |
| 2009/0208552 A1* | 8/2009 | Faucher et al. | 424/423 |
| 2009/0259289 A1* | 10/2009 | Wilson et al. | 623/1.11 |
| 2010/0063571 A1* | 3/2010 | Roach et al. | 623/1.11 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| EP | 1295570 A2 * | 3/2003 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/15106 | 4/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/30487 | 4/2002 |
| WO | WO 2004/023985 | 3/2004 |

OTHER PUBLICATIONS

U.S. Appl. No. 10/317,435, filed Dec. 11, 2002, Hossainy et al.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure In polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants— practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single—chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

International Search Report for PCT/US2007/014331 filed Jun. 19, 2007, mailed Dec. 28, 2007, 13 pgs.

\* cited by examiner

STENT CRIMPING APPARATUS AND METHOD

FIELD OF THE INVENTION

This invention relates to an apparatus for crimping a stent and a method for crimping a stent.

BACKGROUND

A typical stent is a cylindrically shaped device, which holds open and sometimes expands a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

A stent is typically composed of scaffolding that includes a pattern or network of interconnecting structural elements often referred to in the art as struts or bar arms. The scaffolding can be formed from wires, tubes, or sheets of material rolled into a cylindrical shape.

In the case of a balloon expandable stent, the stent is mounted on a balloon connected to a catheter. A typical conventional method of mounting the stent on the balloon is a two-step process. First, the stent is compressed or crimped onto the balloon. Second, the compressed or crimped stent is retained or secured on the balloon. The retained stent should have a sufficiently small diameter so that it can be transported through the narrow passages of blood vessels. The stent must be secured on the balloon during delivery until it is deployed at an implant or treatment site within a vessel in the body of a patient. The stent is then expanded by inflating the balloon. "Delivery" refers to introducing and transporting the crimped stent through a bodily lumen to the treatment site in a vessel. "Deployment" corresponds to the expanding of the crimped stent within the lumen at the treatment site. Delivery and deployment of a stent are accomplished by positioning the stent about one end of a catheter, inserting the end of the catheter through the skin into a bodily lumen, advancing the catheter in the bodily lumen to a desired treatment location, inflating the stent at the treatment location, and removing the catheter from the lumen by deflating the balloon.

The stent should be firmly secured to the balloon to avoid detachment of the stent before it is delivered and deployed in the lumen of the patient. Detachment of a stent from the balloon during delivery and deployment can result in medical complications. A lost stent can act as an embolus that can create a thrombosis and require surgical intervention. For this reason, a stent must be securely attached to the catheter. Stent retention is greatly enhanced by protrusion of the balloon into the interstitial spaces or gaps between stent struts.

Stent retention for a polymer stent is especially challenging. Because polymers generally have lower strength than metals, a polymer stent requires wider struts than a metal stent to achieve the same mechanical strength. As a result, a polymer stent has smaller spaces or gaps between adjacent struts, making it more difficult for a balloon to protrude into the spaces to enhance stent retention. Additionally, a polymer stent may have a similar $T_g$ as the balloon material so that there is a limitation on the use of high temperature to enhance balloon protrusion into stent gaps. When high temperature is used during a crimping process, the stent tends to return to its original dimension and lose its preferred mechanical properties.

SUMMARY

The present invention overcomes the above disadvantage of the prior art. In an preferred embodiment of the present invention, the balloon may be inflated when the stent is crimped onto the balloon, allowing the balloon to extend into the gaps of the stent to enhance stent retention.

In accordance with one aspect of the invention, a method for crimping a stent onto a balloon includes inflating a balloon with a fluid such as a gas or a liquid, sliding a stent over the inflated balloon, crimping the stent onto the balloon, and controlling the pressure inside the balloon below a given value when the stent is being crimped onto the balloon.

In a preferred embodiment of the invention, the step of controlling includes releasing the fluid inside the balloon when the pressure exceeds the given value so that the pressure inside the balloon does not exceed the given value.

In another preferred embodiment of the invention, the step of releasing includes using a pressure release valve to control the fluid inside the balloon below the given value.

In still another preferred embodiment of the invention, the method includes placing the stent and balloon in a crimper before the stent is crimped onto the balloon.

In a further embodiment of the invention, the method includes soaking the balloon in a solvent to soften the balloon. The solvent may be acetone.

In accordance with another aspect of the invention, a method for crimping a stent onto a balloon includes sliding a stent over a balloon, placing the stent and balloon in a stent crimper, inflating the balloon with a fluid such as a gas or a liquid, crimping the stent onto the balloon, and controlling the pressure inside the balloon below a given value when the stent is being crimped onto the balloon.

In a preferred embodiment of the invention, the method includes reducing the crimper's inner diameter to the outer diameter of the stent before inflating the balloon with the fluid.

In another preferred embodiment of the invention, the step of controlling includes releasing the fluid inside the balloon when the pressure exceeds the given value so that the pressure inside the balloon does not exceed the given value.

In still another preferred embodiment of the invention, the step of releasing includes using a pressure release valve to control the fluid inside the balloon below the given value.

In a further embodiment of the invention, the method includes soaking the balloon in a solvent to soften the balloon. The solvent may be acetone.

In accordance with a further aspect of the invention, a stent crimping apparatus includes means for inflating a balloon with a fluid such as a gas or a liquid, means for crimping the stent onto the balloon, and means for controlling the pressure inside the balloon below a given value when the stent is being crimped onto the balloon.

DETAILED DESCRIPTION OF THE INVENTION

Those of ordinary skill in the art will realize that the following description of the invention is illustrative only and not in any way limiting. Other embodiments of the invention will readily suggest themselves to such skilled persons based on the disclosure herein. All such embodiments are within the scope of this invention.

Figure 1:
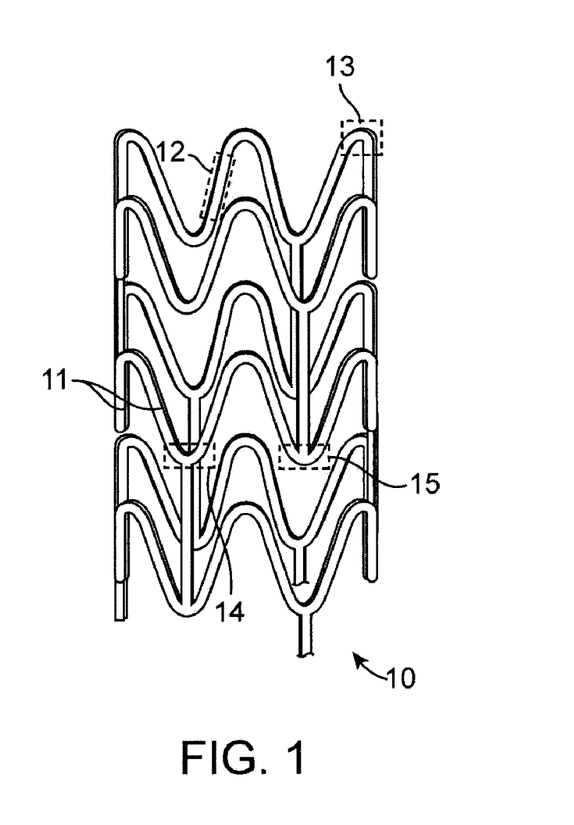
FIG. 1 shows a perspective view of a stent.

FIG. 1 illustrates a stent 10 that includes a number of interconnecting structural elements or struts 11. In general, the pattern of the stent struts is designed so that the stent can be radially compressed and expanded. The stent may include portions of struts that are straight or relatively straight, an example being a straight portion designated by reference numeral 12. The stent may also include portions of struts that are bent, such as the portions designated by reference numerals 13, 14, and 15. The bent portions 13, 14, and 15 may bend further when the stent 10 is crimped radially inwardly. The bent portions 13, 14, and 15 may bend less when the stent 10 is expanded radially outwardly.

A stent, as fabricated, is uncrimped and may have an outside diameter that is typically from about 1 mm and to about 4 mm. When the stent is crimped, the structural elements deform allowing the stent to decrease in diameter. The deformation occurs primarily at the bending elements. The balloon, when mounted on a catheter, may have an outside diameter of between about 0.7 mm and 0.8 mm. The outside diameter of a crimped stent may be approximately the same as the outside diameter of the balloon.

In some embodiments, a stent of the present invention may be formed from a tube by laser cutting the pattern of structural elements in the tube. The stent may also be formed by laser cutting a polymeric or metallic sheet, rolling the pattern into the shape of the cylindrical stent, and providing a longitudinal weld to form the stent. Other methods of forming stents are well known and include chemically etching a polymeric or metallic sheet and rolling and then welding it to form the stent. A polymeric or metallic wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

A stent can be made from one or more suitable materials. For example, a stent may be made from a metallic material. Alternatively, a stent may be made from a polymeric material. A stent may include a biodegradable material, such as a biodegradable polymer or metal. The biodegradable material may be a pure or substantially pure biodegradable polymer or metal. Alternatively, the biodegradable material may be a mixture of at least two types of biodegradable polymers and metals.

Representative examples of polymers that may be used to fabricate embodiments of stents, or more generally, implantable medical devices include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alpha-olefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

Figure 2:
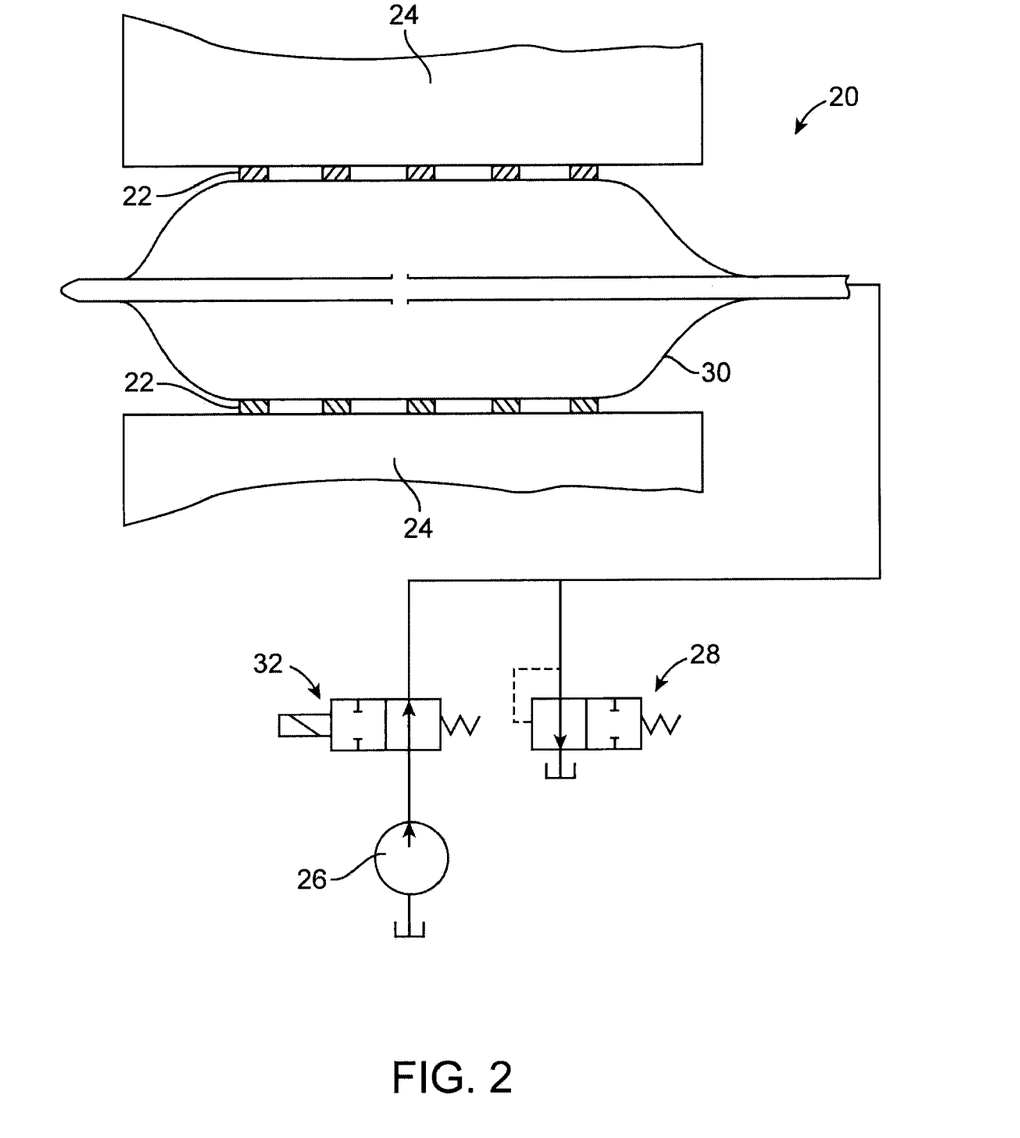
FIG. 2 shows one apparatus for crimping a stent according to the present invention.

FIG. 2 illustrates one apparatus 20 for crimping a stent 22 according to the present invention. In the present invention, to "crimp" a stent is to compress the stent radially inward to reduce its diameter. The apparatus 20 may include one or more crimping elements 24, a source 26 for pressurized fluid, and a pressure control device 28.

The crimping elements 24 can be used to crimp the stent 22. The crimping elements 24 may be any of the known crimping devices that can move radially to crimp the stent 22. Such crimping elements (or device) are well known in the art and will not be described in detail here.

The pressurized fluid source 26 can be used to supply pressurized fluid, such as pressurized gas or liquid, to inflate a balloon 30, on which the stent 22 is mounted. The balloon 28 may be part of a catheter (not shown). The pressurized fluid source 26 may be any device that can supply pressurized fluid, such as a pump or an accumulator. In the illustrated embodiment, the pressurized fluid source 26 is a pump 26. Preferably, a valve 32 is provided that can shut off the pressurized fluid supplied by the pump 26 to the balloon 30.

The pressure control device 28 may be used to control the pressure inside the balloon 30. For example, the pressure control device 28 may keep the pressure inside of the balloon 30 below a predetermined value. The pressure control device may be any suitable device for achieving this purpose. In the illustrated embodiment, the pressure control device 28 is a pressure relief valve 28.

To crimp the stent 22 on the balloon 30 in accordance with one method of the present invention, the balloon 30 is first inflated using the pressurized fluid supplied by the pump 26 (or any other suitable pressurized fluid source). To soften the balloon 30, the balloon 30 may be soaked in a solvent, such as acetone, for a predetermine period of time. After the stent 22 at a first diameter value has been slid on the inflated balloon 30, the stent 22 and balloon 30 are placed in the stent crimping apparatus 20. Next, the crimping elements 24 may radially compress the stent 22 to reduce the stent's diameter to a second diameter value while the balloon remains inflated. During crimping, the balloon pressure may be kept at or below a first pressure value by the pressure relief valve 28. If the pressure inside the balloon 30 is above the first pressure value, the pressure relief valve 28 opens to discharge the pressurized fluid inside the balloon until the pressure reaches or is below the first pressure value. After the diameter of the stent has been reduced to the second diameter value, the balloon pressure may be kept at the first pressure value for a first period of time. Then the pressure inside the balloon may be released for a second period of time. Next the balloon is inflated again to a second pressure value, and the stent is crimped again until its diameter reaches a third diameter value. The balloon pressure may be kept at the second pressure value for a third period of time. Then the pressure inside the balloon may be released, and the stent and balloon may be removed from the stent crimping apparatus 20.

To crimp the stent 22 on the balloon 30 in accordance with another method of the present invention, the stent 22 is first slid on the balloon 30 without the balloon 30 being inflated. To soften the balloon 30, the balloon 30 may be soaked in a solvent, such as acetone, for a predetermine period of time. Then the stent 22 and balloon 30 are placed in the stent crimping apparatus 20. Next the stent 22 may be radially compressed from a first diameter value to a second diameter value while the balloon is not inflated. After the diameter of the stent has been reduced to the second diameter value, the balloon may be inflated to a first pressure value for a first period of time. Then the stent is crimped again until its diameter reaches a third diameter value. The balloon pressure may be kept at the first pressure value for a second period of time. Then the pressure inside the balloon may be released, and the stent and balloon may be removed from the stent crimping apparatus 20.

Figure 3:
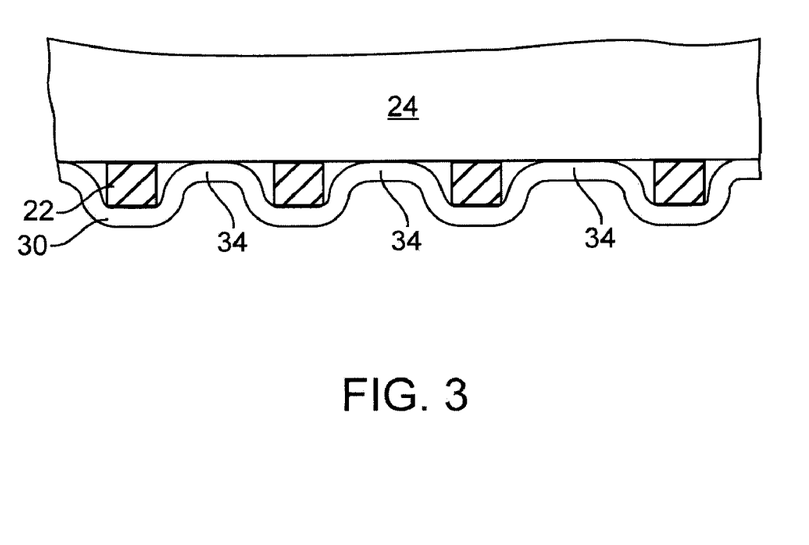
FIG. 3 shows portions of a balloon extending into the gaps of a stent.

FIG. 3 shows that after the stent 22 has been crimped onto the balloon 30 using a method of the present invention, portions 34 of the balloon 30 extend into the gaps of the stent 22.

The following are two examples of stent crimping using a method of the present invention.

Example I

The outer diameter of a pre-crimp stent is 0.135 inches. The balloon is inflated to 39 psi, and the stent is mounted on the balloon. The stent and balloon are placed in a stent crimping apparatus, and the stent is crimped to 0.090 inches while the balloon pressure is kept at 39 psi. Next, the balloon pressure is kept at 39 psi for 20 seconds. Afterwards, the balloon may be deflated for a period of time. The crimper then reduces the outer diameter of the stent to 0.045 inches for 50 seconds without balloon pressure. The balloon is inflated again for 20 seconds under 39 psi. Then the balloon pressure is reduced to zero for 20 seconds. Finally, the stent and balloon are removed from the crimper.

Example II

The outer diameter of an uncrimped stent is 0.084 inches. The uncrimped stent is placed in a crimper, and the crimper's inner diameter is reduced to 0.084 inches, which is the outer diameter of the uncrimped stent. Next, the balloon is inflated under 30 psi pressure for 20 seconds. The crimper then reduces the outer diameter of the stent to 0.032 inches under 30 psi for five seconds and then for 45 seconds without balloon pressure. The balloon is inflated again for 25 seconds under 30 psi. Then the balloon pressure is reduced to zero for 10 seconds. Finally, the stent and balloon are removed from the crimper.

While particular embodiments of the present invention have been shown and described, it will be obvious to those skilled in the art that changes and modifications can be made without departing from this invention in its broader aspects.

What is claimed is:

1. A method for crimping a stent onto a balloon, comprising:
   inflating a balloon with a fluid to a first pressure value;
   sliding a stent at a first diameter over the inflated balloon;
   crimping the stent to a second diameter that is less than the first diameter onto the balloon;
   after crimping the stent to the second diameter, releasing the pressure from inside the balloon so that the balloon is deflated;
   inflating the balloon that is deflated to a second pressure value;
   crimping the stent to a third diameter that is less than the second diameter after inflating the balloon to the second pressure value; and
   controlling the pressure inside the balloon below the first pressure value when crimping to the second diameter and below the second pressure value when crimping to the third diameter.

2. The method of claim 1, wherein the step of controlling includes releasing the fluid inside the balloon when the pressure exceeds the first pressure value or second pressure value so that the pressure inside the balloon does not exceed the first pressure value or second pressure value, respectively.

3. The method of claim 2, wherein the step of releasing includes using a pressure release valve to control the fluid inside the balloon below the first or second pressure value.

4. The method of claim 1, further comprising placing the stent and balloon in a crimper before the stent is crimped to the second diameter onto the balloon.

5. The method of claim 1, further comprising soaking the balloon in a solvent to soften the balloon.

6. The method of claim 5, wherein the solvent is acetone.

7. The method of claim 1, wherein after crimping the stent to the second diameter, the balloon pressure is kept at the first pressure value for a period of time.

8. The method of claim 1, wherein after crimping the stent to the third diameter, the balloon pressure is kept at the second pressure value for a period of time.

9. The method of claim 1, further comprising releasing the pressure from the balloon after crimping the stent to the third diameter.

10. The method of claim 1, wherein the stent comprises a network of interconnecting struts with gaps between adjacent struts, wherein after the crimping steps the balloon extends into the gaps to enhance stent retention.

11. The method of claim 1, wherein the balloon is deflated for a period of time.

12. A method for crimping a stent onto a balloon, comprising:
   sliding a stent at a first diameter over a balloon that is not inflated;
   placing the stent and balloon that is not inflated in a stent crimper;
   crimping the stent to a second diameter that is less than the first diameter while the balloon is not inflated;
   inflating the balloon to a pressure value after crimping the stent to the second diameter;
   crimping the stent to a third diameter that is less than the second diameter after inflating the balloon; and controlling the pressure inside the balloon below the pressure value when the stent is being crimped onto the balloon.

13. The method of claim 12, further comprising reducing an inner diameter of the crimper to the outer diameter of the stent before inflating the balloon with the fluid.

14. The method of claim 12, wherein the step of controlling includes releasing the fluid inside the balloon when the pressure exceeds the pressure value so that the pressure inside the balloon does not exceed the pressure value.

15. The method of claim 14, wherein the step of releasing includes using a pressure release valve to control the fluid inside the balloon below the pressure value.

16. The method of claim 12, further comprising soaking the balloon in a solvent to soften the balloon.

17. The method of claim 16, wherein the solvent is acetone.

18. The method of claim 12, wherein after inflating the balloon and before crimping the stent to the third diameter, the balloon pressure is kept at the pressure value for a period of time.

19. The method of claim 12, wherein after crimping the stent to the third diameter, the balloon pressure is kept at the pressure value for a period of time.

20. The method of claim 12, further comprising releasing the pressure from the balloon after crimping the stent to the third diameter.

21. The method of claim 12, wherein the stent comprises a network of interconnecting struts with gaps between adjacent struts, wherein after the crimping steps the balloon extends into the gaps to enhance stent retention.

* * * * *